United States Patent
Hayashi et al.

(10) Patent No.: US 6,823,042 B2
(45) Date of Patent: Nov. 23, 2004

(54) APPARATUS FOR X-RAY ANALYSIS AND APPARATUS FOR SUPPLYING X-RAYS

(75) Inventors: Seiichi Hayashi, Yokohama (JP); Jimpei Harada, Tokyo (JP); Sadayuki Takahashi, Tokyo (JP); Masaru Kuribayashi, Akishima (JP)

(73) Assignee: Rigaku Corporation, Akishima (JP)

( * ) Notice: Subject to any disclaimer, the term of this patent is extended or adjusted under 35 U.S.C. 154(b) by 68 days.

(21) Appl. No.: 10/188,398

(22) Filed: Jul. 2, 2002

(65) Prior Publication Data

US 2003/0007599 A1 Jan. 9, 2003

(30) Foreign Application Priority Data

Jul. 3, 2001 (JP) ........................................ 2001-202762

(51) Int. Cl.[7] ................................................. G21K 1/06
(52) U.S. Cl. ........................................... 378/84; 378/85
(58) Field of Search ............................. 378/64, 84, 85, 378/138, 145, 147, 156, 159

(56) References Cited

U.S. PATENT DOCUMENTS

| | | | | |
|---|---|---|---|---|
| 4,145,616 A | | 3/1979 | Tanabe | |
| 4,525,853 A | * | 7/1985 | Keem et al. | 378/84 |
| 4,607,380 A | * | 8/1986 | Oliver | 378/138 |
| 5,799,056 A | * | 8/1998 | Gutman | 378/84 |
| 6,014,423 A | * | 1/2000 | Gutman et al. | 378/85 |
| 6,041,099 A | * | 3/2000 | Gutman et al. | 378/85 |
| 6,249,566 B1 | * | 6/2001 | Hayashi et al. | 378/85 |
| 6,504,902 B2 | * | 1/2003 | Iwasaki et al. | 378/84 |

* cited by examiner

*Primary Examiner*—Edward J. Glick
*Assistant Examiner*—Allen C. Ho
(74) *Attorney, Agent, or Firm*—Frishauf, Holtz, Goodman & Chick, P.C.

(57) ABSTRACT

Apparatus for X-ray analysis has a combination of a rotating target X-ray tube and a composite monochromator. The composite monochromator has a first and a second elliptic monochromators joined with each other side by side. Each of the elliptic monochromators has a first focal point at which an X-ray focal spot on a target of the X-ray tube is disposed. Each of the elliptic monochromators has a synthetic multilayered thin film whose d-spacing varies continuously along an elliptic-arc. The shortest distance between the X-ray focal spot and the composite monochromator is set to 40 to 100 mm. Under the shortest distance condition, the effective focal spot size on the target is set to 40 to 100 micrometers to obtain the maximum X-ray intensity on a sample to be analyzed.

8 Claims, 18 Drawing Sheets

FIG. 14

$$W = \frac{4.2\, S(T_m - T_o)}{\dfrac{2}{\pi}\sqrt{\dfrac{t}{DNC\rho\sigma}} + \dfrac{e}{C}\dfrac{t}{\pi D}} \quad \cdots (1)$$

$$S = FL * t = 10t * t \quad \cdots (2)$$

W : MAXIMUM INPUT POWER (W)

FL : LENGTH OF FOCAL POINT (cm) = 10t t : WIDTH OF FOCAL POINT (cm) = FOCAL SPOT SIZE $T_m$ : MELTING POINT OF TARGET MATERIAL (°C) = 1084

$T_o$ : TEMPERATURE OF COOLED SURFACE (°C) = 100

C : THERMAL CONDUCTIVITY OF TARGET MATERIAL (cal/cm.sec.°C) = 0.76

$\rho$ : DENSITY OF TARGET MATERIAL (g/cm$^3$) = 8.94

$\sigma$ : SPECIFIC HEAT OF TARGET MATERIAL (cal/g.°C)

= 0.12

N : ROTATIONAL SPEED (rpm) = 6000

D : DIAMETER OF TARGET (cm) = 10 e : THICKNESS OF TARGET (cm) = 0.2

FIG. 15

$$y = b\sqrt{1 - \frac{(x-a)^2}{a^2}} \quad \cdots (3)$$

$$\frac{dy}{dx} = \frac{-b(x-a)}{a^2\sqrt{1 - \frac{(x-a)^2}{a^2}}} \quad \cdots (4)$$

$$\text{SLOPE (deg)} = \arctan\left[\frac{-b(x-a)}{a^2\sqrt{1 - \frac{(x-a)^2}{a^2}}}\right]\frac{180}{\pi} \quad \cdots (5)$$

$$\text{ELEVATION ANGLE (deg)} = \arctan\left[\frac{y}{(x-f)}\right]\frac{180}{\pi} \quad \cdots (6)$$

$$\text{INCIDENCE ANGLE } \theta = \text{ELEVATION ANGLE} - \text{SLOPE} \quad \cdots (7)$$

FIG. 16

$$2d\sin\theta = \lambda \qquad \cdots(8)$$

$$\theta_{max} = \arcsin\left[\frac{\lambda}{2\,d_{max}}\right]\frac{180}{\pi} \qquad \cdots(9)$$

$$\theta_{min} = \arcsin\left[\frac{\lambda}{2\,d_{min}}\right]\frac{180}{\pi} \qquad \cdots(10)$$

| t | a | b | L4 | $\alpha^2$ |
|---|---|---|---|---|
| 0.01 | 1860 | 10 | 120 | 1.18869 E-4 |
| 0.015 | 1260 | 10 | 120 | 1.78105 E-4 |
| 0.02 | 960 | 10 | 120 | 2.37218 E-4 |
| 0.025 | 780 | 10 | 120 | 2.96212 E-4 |
| 0.03 | 660 | 9.7 | 120 | 3.34131 E-4 |
| 0.035 | 574.286 | 9 | 120 | 3.35316 E-4 |
| 0.04 | 510 | 8.4 | 120 | 3.33564 E-4 |
| 0.045 | 460 | 8 | 120 | 3.37268 E-4 |
| 0.05 | 420 | 7.6 | 120 | 3.40785 E-4 |
| 0.06 | 360 | 6.5 | 120 | 2.98719 E-4 |
| 0.07 | 317.143 | 5.2 | 120 | 2.22762 E-4 |
| 0.08 | 285 | 4.2 | 120 | 1.65872 E-4 |
| 0.09 | 260 | 3.5 | 120 | 1.29422 E-4 |
| 0.1 | 240 | 3 | 120 | 1.05519 E-4 |
| 0.15 | 257.831 | 3.5 | 171.887 | 4.76392 E-5 |
| 0.2 | 286.479 | 4.1 | 229.183 | 2.68356 E-5 |
| 0.25 | 315.127 | 4.6 | 286.479 | 1.70901 E-5 |
| 0.3 | 343.775 | 5.1 | 343.775 | 1.20821 E-5 |
| 0.35 | 372.423 | 5.5 | 401.07 | 8.81754 E-6 |
| 0.4 | 401.07 | 5.9 | 458.366 | 6.78260 E-6 |

US 6,823,042 B2

APPARATUS FOR X-RAY ANALYSIS AND APPARATUS FOR SUPPLYING X-RAYS

BACKGROUND OF THE INVENTION

This invention relates to apparatus for X-ray analysis which uses a composite monochromator having combined two elliptic monochromators, the composite monochromator being arranged between an X-ray source and a sample, and relates to apparatus for supplying X-rays which uses a composite monochromator having combined two elliptic monochromators.

U.S. Pat. No. 6,249,566 discloses apparatus for X-ray analysis which uses a composite monochromator having combined two elliptic monochromators, the composite monochromator being arranged between an X-ray source and a sample. The two elliptic monochromators are joined with each other side by side. Each of the two elliptic monochromators has a reflection surface made of a synthetic multilayered thin film whose period or d-spacing varies continuously along an elliptic-arc. The X-ray source is a microfocus X-ray source having an effective focal spot size of less than 30 micrometers.

Since the prior-art apparatus for X-ray analysis mentioned above uses the microfocus X-ray source having a focal spot size of less than 30 micrometers, even if the distance between the X-ray source and the monochromator becomes smaller (preferably less than 30 mm), the breadth of incidence angle, which depends upon the effective focal spot size of the X-ray source, becomes satisfactorily within the range of the half-value width of the diffraction peak of the elliptic monochromator, so that the X-rays reaching the elliptic monochromator are utilized effectively with no loss. Furthermore, since the distance between the X-ray source and the elliptic monochromator can be smaller, the capture angle of incident X-rays on the elliptic monochromator is increased, so that the X-ray intensity focused on the sample can be greatly increased.

Since the prior-art apparatus for X-ray analysis mentioned above has a monochromator coming closer to the X-ray source than 30 mm preferably, the X-ray source to be used is of a stationary-target type. The microfocus target of the stationary type, however, has a limitation in receiving power which is supplied to an X-ray tube, so that it is difficult to increase the input power in order to obtain a higher X-ray intensity focused on the sample.

SUMMARY OF THE INVENTION

It is an object of the present invention to provide apparatus for X-ray analysis and apparatus for supplying X-rays each having a combination of a rotating target X-ray tube and the above-mentioned composite monochromator under an optimum condition in which a higher X-ray intensity focused on a sample can be expected.

Apparatus for X-ray analysis according to the invention has an X-ray source generating an X-ray beam which is reflected by a monochromator and thereafter incident on a sample, and is characterized below. The X-ray source is a rotating target X-ray tube having a rotating target which has an effective focal spot size of 40 to 100 micrometers. The monochromator is a composite monochromator having a first and a second elliptic monochromators joined with each other side by side. Each of the elliptic monochromators has a first focal point at which the X-ray focal spot on the target is disposed, and a second focal point at which the sample is to be disposed. Each of the first and second elliptic monochromators has a reflection surface made of a synthetic multilayered thin film in which layer boundaries, which contribute to diffraction, are parallel to the reflection surface and d-spacing varies continuously along an elliptic-arc so as to satisfy the Bragg's equation for X-rays with a predetermined wavelength at any point of the reflection surface. The shortest distance between the X-ray focal spot on the target and the composite monochromator is 40 to 100 mm.

Since the apparatus for X-ray analysis according to the invention has a combination of the rotating target X-ray tube and the composite monochromator in which the effective focal spot size on the target is 40 to 100 micrometers and the shortest distance between the X-ray focal spot on the target and the composite monochromator is 40 to 100 mm, an X-ray intensity focused on the sample is increased with the maximum efficiency.

This invention may be applied to not only apparatus for X-ray analysis, in which X-rays are incident on a sample to be analyzed, but also apparatus for sullying X-rays in other applications. The apparatus for supplying X-rays may be used, for example, for (1) apparatus for X-ray analysis, (2) apparatus for X-ray irradiation in the fields of material processing, medical care and so on, and (3) apparatus for X-ray lithography. With the apparatus for supplying X-rays according to the invention, the X-ray source, which is disposed at the first focal point of the composite monochromator, generates an X-ray beam which is collected and reflected by the composite monochromator. The composite monochromator can re-generate the X-ray beam toward the second focal point of the composite monochromator with a high intensity.

BRIEF DESCRIPTION OF THE DRAWINGS

FIG. 14 shows equations to calculate the maximum input power of the rotating target;

FIG. 15 shows some equations to calculate an elliptic curve, a slope at each position on the ellipse, an elevation angle from the focal point F1, and an incidence angle;

FIG. 16 shows the Bragg's equation and equations to calculate incidence angles corresponding to the maximum and the minimum d-spacing of the synthetic multilayered thin film;

FIG. 18 shows a table of the calculation result at L1=80 mm.

DETAILED DESCRIPTION OF THE PREFERRED EMBODIMENTS

Figure 1:
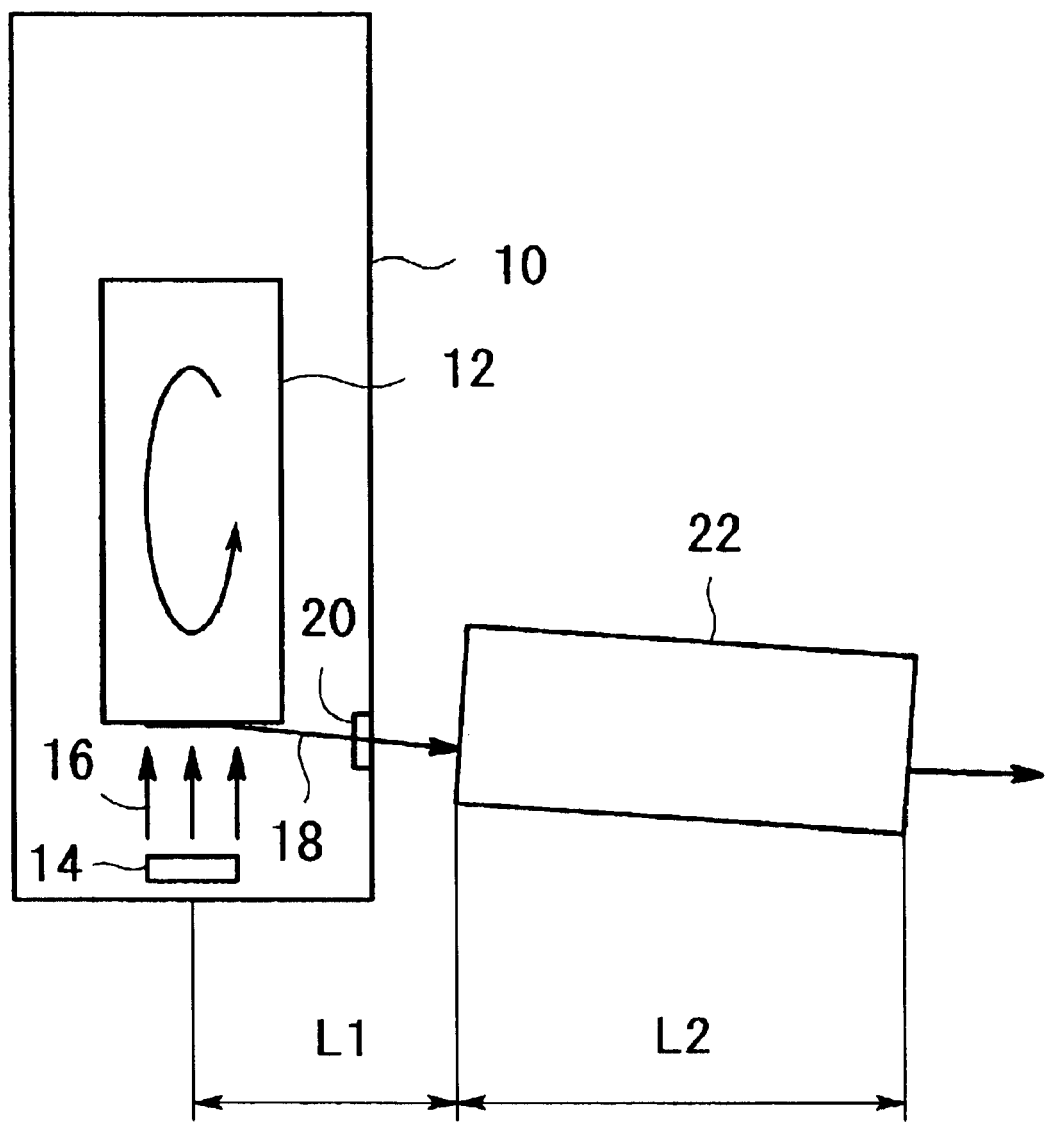
FIG. 1 is a plan view illustrating schematically one embodiment of the apparatus for X-ray analysis according to the invention.

Referring to FIG. 1, a rotating target X-ray tube 10 has a rotating target 12. An electron gun 14 emits an electron beam 16 which is incident on the peripheral surface of the target 12 to emit an X-ray beam 18 from the electron beam irradiation region (X-ray focal spot). The X-ray beam 18 is taken out through a beryllium window 20 and incident on a composite monochromator 22. The take-off angle of the X-ray beam 18 is about 6 degrees with respect to the target surface. The X-ray beam 18 is made monochromatic and focused by the composite monochromator 22 and thereafter incident on a small irradiation spot on a sample. The shortest distance between the center of the focal spot on the target 12 and the composite monochromator 22 is represented by L1, and the length of the composite monochromator 22 is represented by L2.

Figure 2:
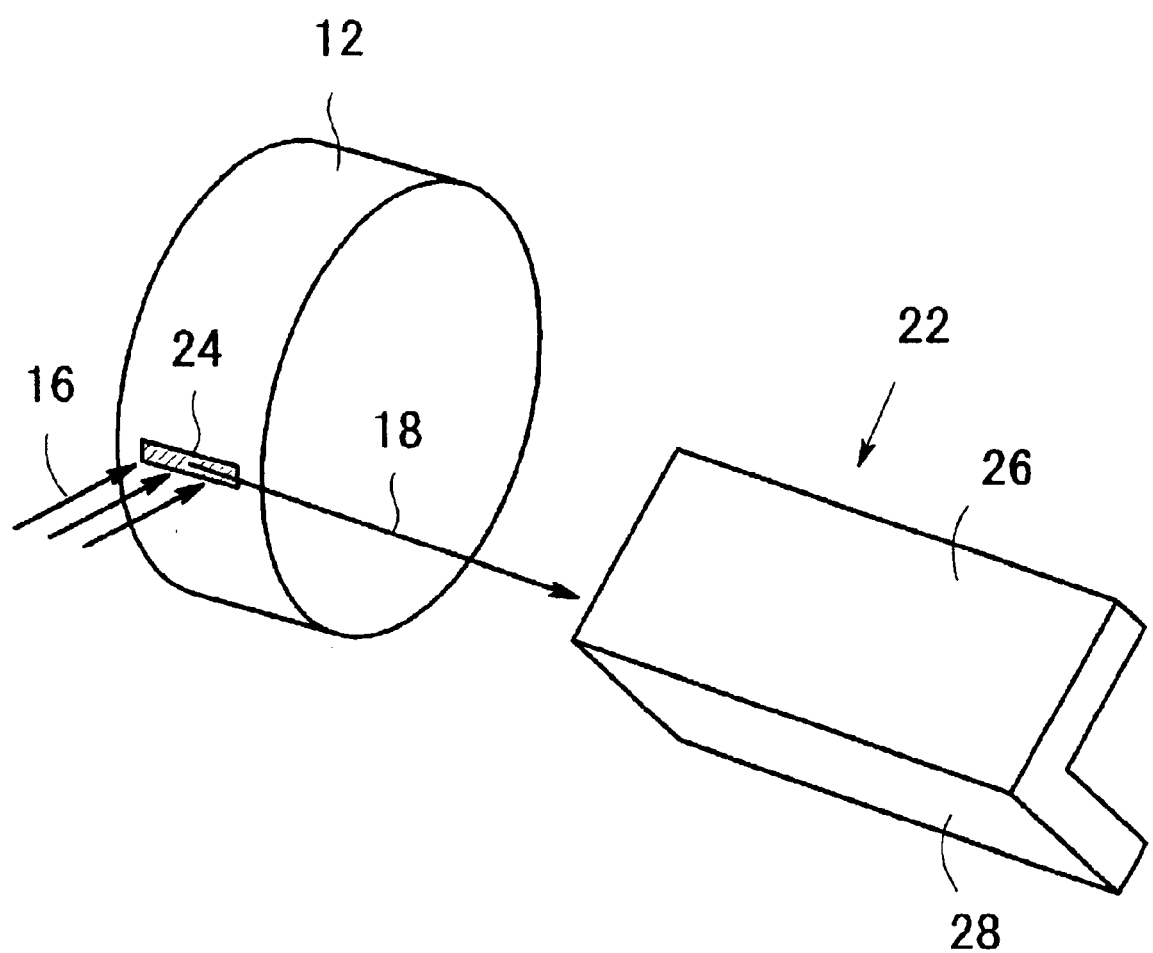
FIG. 2 is a perspective view illustrating a positional relationship between a rotating target and a composite monochromator shown in FIG. 1.

Referring to FIG. 2, a cylindrical target 12 has a peripheral surface on which a long narrow focal spot 24 is formed with a lengthwise direction parallel to the axis of rotation of the target 12. The composite monochromator 22 is comprised of the first elliptic monochromator 26 and the second elliptic monochromator 28 joined with each other side by side at right angles. Each of the two elliptic monochromators has a reflection surface made of a synthetic multilayered thin film in which layer boundaries, which contribute to diffraction, are parallel to the reflection surface and a period (it corresponds to crystal d-spacing) varies continuously along an elliptic-arc. The shape and the action of such a composite monochromator are disclosed in detail in U.S. Pat. No. 6,249,566.

Figure 3:
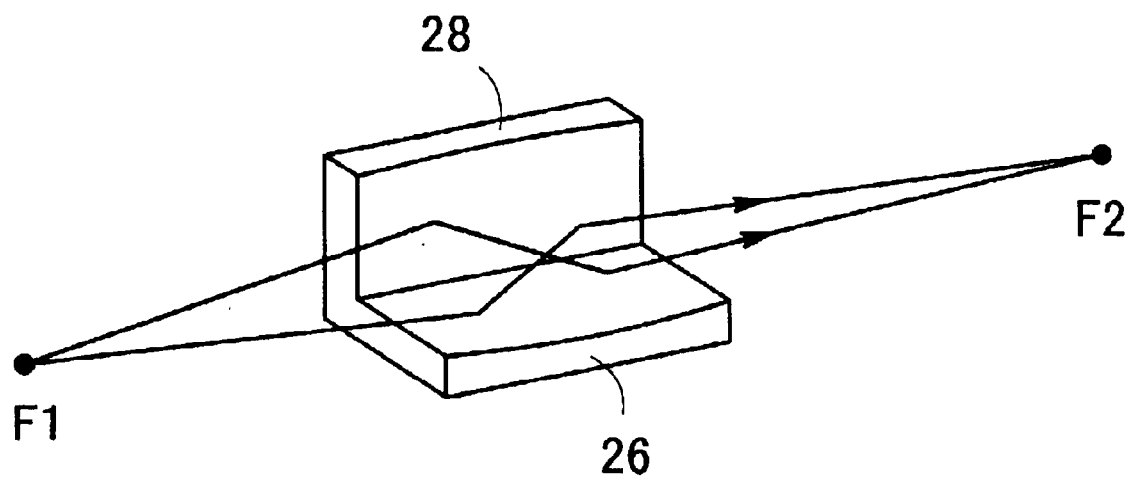
FIG. 3 is a perspective view illustrating the action of the composite monochromator.

Referring to FIG. 3, each of the first elliptic monochromator 26 and the second elliptic monochromator 28 has the first focal point F1 at which the X-ray focal spot on the target is disposed, and the second focal point F2 at which the X-ray irradiation region on the sample is disposed. The X-ray beam, which is generated at the first focal point F1, is reflected first at the first elliptic monochromator 26 and reflected second at the second elliptic monochromator 28 and thereafter incident on the sample which is disposed at the second focal point F2. Alternatively, the X-ray beam is reflected first at the second elliptic monochromator 28 and reflected second at the first elliptic monochromator 26 and thereafter incident on the sample. The first and the second elliptic monochromators 26 and 28 have the same shape basically, and therefore only the first elliptic monochromator 26 will be described below.

Figure 4:
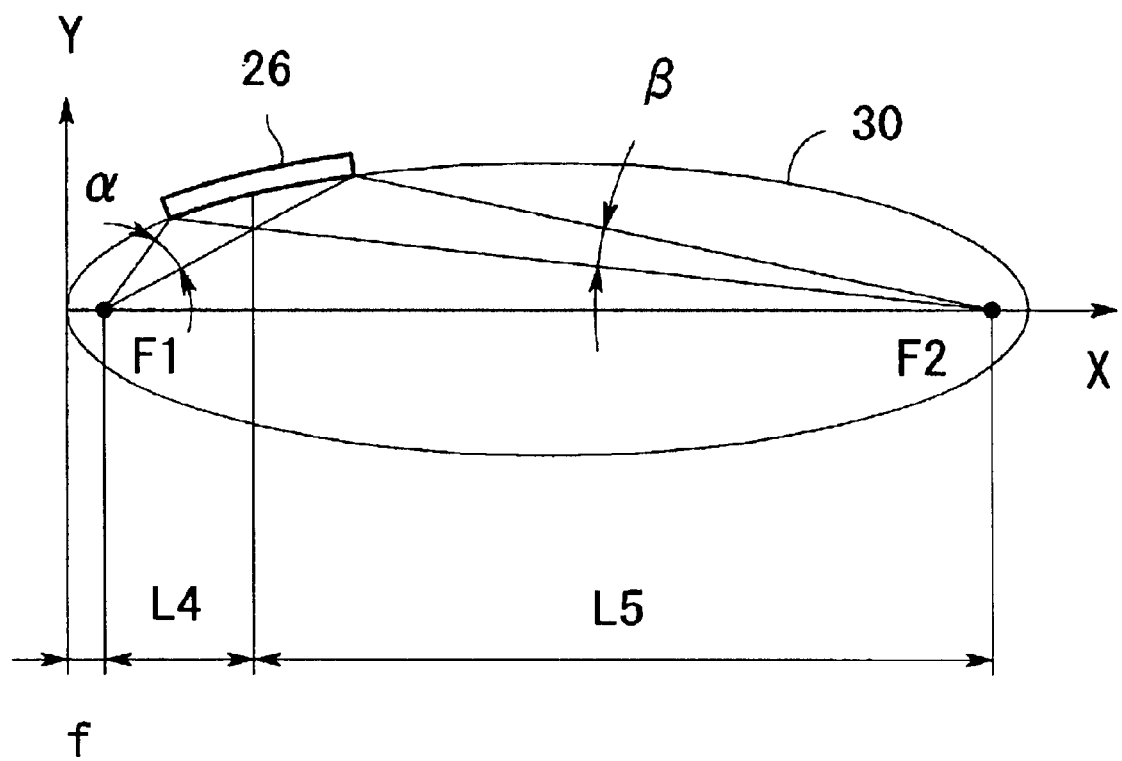
FIG. 4 illustrates a principle with which the elliptic monochromator focuses X-rays.

Referring to FIG. 4, the first elliptic monochromator 26 has a reflection surface made of an elliptic-arc surface which is a trace of an elliptic-arc, i.e., a part of the ellipse 30, translated in a direction perpendicular to the drawing sheet. The X-ray beam from the first focal point F1 of the ellipse 30 reaches the first elliptic monochromator 26 with a divergence angle $\alpha$ which represents an angle with which the elliptic monochromator 26 captures the X-ray beam, and thus the angle $\alpha$ is referred to hereafter a capture angle. The larger the capture angel $\alpha$, the higher the efficiency of the X-ray use. On the other hand, the X-ray beam from the first elliptic monochromator 26 reaches the second focal point F2 with a convergence angle $\beta$ which represents variation of the X-ray incidence angle on the sample. Generally a small convergence angle $\beta$ is preferable in the X-ray analysis for the sample.

Next, the effective focal spot size of the X-ray focal spot on the target will be described. The effective focal spot size is defined by a focal spot size on the target as seen from the X-ray take-off direction, noting that the maximum diametrical size should be the effective focal spot size. For example, assuming that a long narrow focal spot 24 of 1 mm×0.1 mm is formed on the target 12 as shown in FIG. 2 and a line-focus X-ray beam is taken out from it with the take-off angle of about 6 degrees, the apparent focal spot region becomes about 0.1 mm×0.1 mm and the effective focal spot size is 0.1 mm.

Using a combination of the rotating target and the composite monochromator, it is found that there is the optimum focal spot size on the target after consideration of various requirements. That is, it is found that when the maximum focal spot size is selected an X-ray intensity on the sample (i.e., a total intensity of X-rays impinging on the sample) becomes highest. The procedure to obtain the optimum conditions and its optimum result will now be described in detail below. In the first place, the following items (1) to (5) have been considered.

(1) Relationship Between Focal Spot Size on Target and Maximum Input Power

Figure 9:
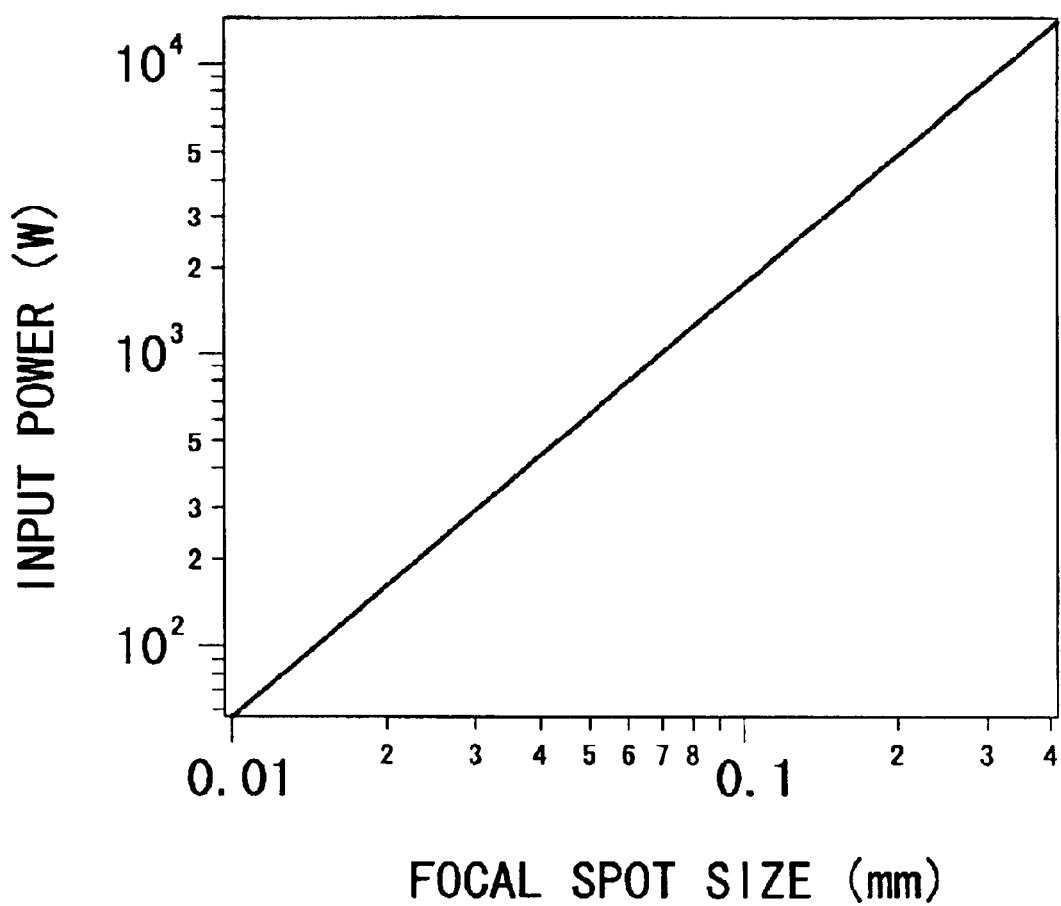
FIG. 9 is a graph showing a relationship between a focal spot size and the maximum input power.

A relationship is well known between a focal spot size t on the rotating target and the possible maximum input power W as shown in a graph of FIG. 9. The graph is obtained from an equation (1) in FIG. 14. The equation (1) is to calculate the maximum input power W (i.e., allowable load) and has been established taking into account the allowable thermal load to the target. Assuming that the material of the target is copper, the rotational speed is 6,000 rpm, the target diameter is 10 cm, and the target thickness (the thickness from the outer surface to the water-cooled inner surface) is 0.2 cm, the maximum input power W depends upon the width t of the focal spot on the target (i.e., the effective focal spot size), noting that the length FL of the focal spot is assumed to be ten times the width t. As seen from the graph of FIG. 9, the larger the focal spot size, the higher the maximum input power.

(2) Condition Under Restriction in Manufacturing Synthetic Multilayered Thin Film The elliptic monochromator or synthetic multilayered thin film mirror is under restriction in manufacturing it, so that the length L2 (see FIG. 1) of the monochromator 22 is set to 80 mm. The d-spacing of the synthetic multilayered thin film, which makes the reflection surface, is determined so that its maximum value, dmax, is less than 5.0 nanometers and its minimum value, dmin, is more than 2.5 nanometers. With the elliptic monochromator having a multilayered thin film whose d-spacing varies continuously along an elliptic-arc, if the d-spacing value is within a range of 2.5 to 5.0 nanometers, this multilayered thin film can be manufactured. On the other hand, the X-ray diffraction occurs at the reflection surface only when an equation (8) in FIG. 16 or Bragg's equation is satisfied, where d is the d-spacing of the synthetic multilayered thin film, $\lambda$ is the wavelength of X-rays, and $\theta$ is the X-ray incidence angle on the reflection surface. Using the rotating target whose material is copper, CuK $\alpha$ rays has a wavelength $\lambda$ of 0.154 nanometers. The maximum value dmax and the minimum value dmin of the d-spacing of the synthetic multilayered thin film can be converted to the incidence angle $\theta$ with the use of the Bragg's equation, the result being equations (9) and (10) in FIG. 16.

(3) Requirement Regarding Acceptable Receiving Angle of Reflection Surface

Figure 5:
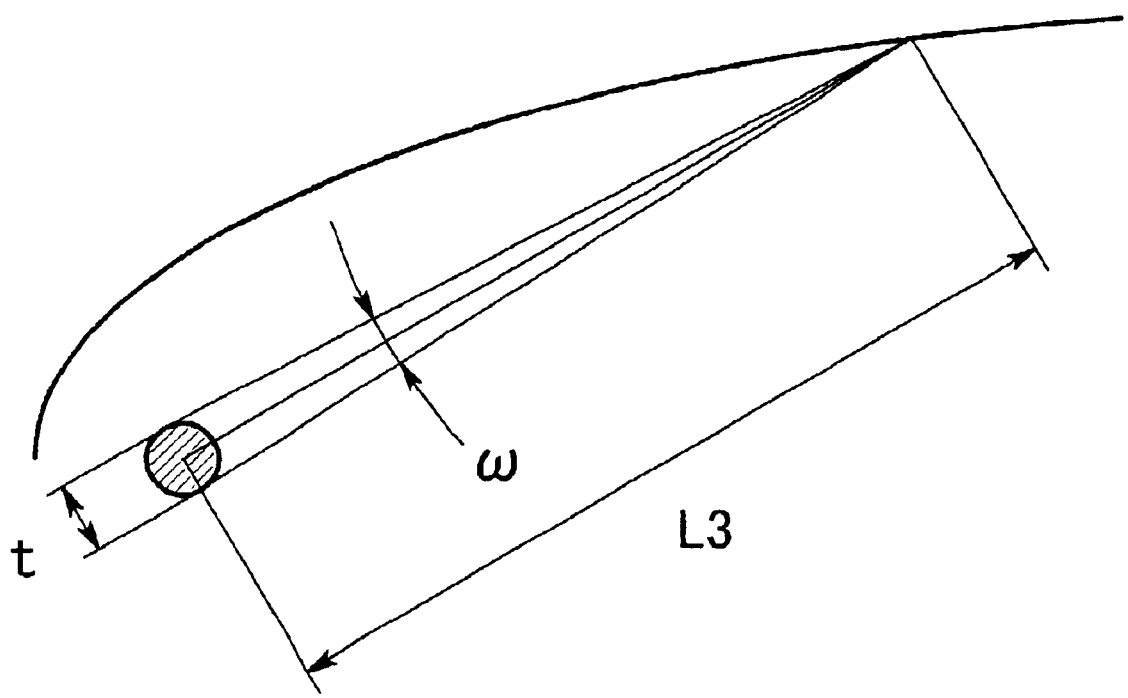
FIG. 5 illustrates an acceptable receiving angle of the reflection surface of the elliptic monochromator.
Figure 6:
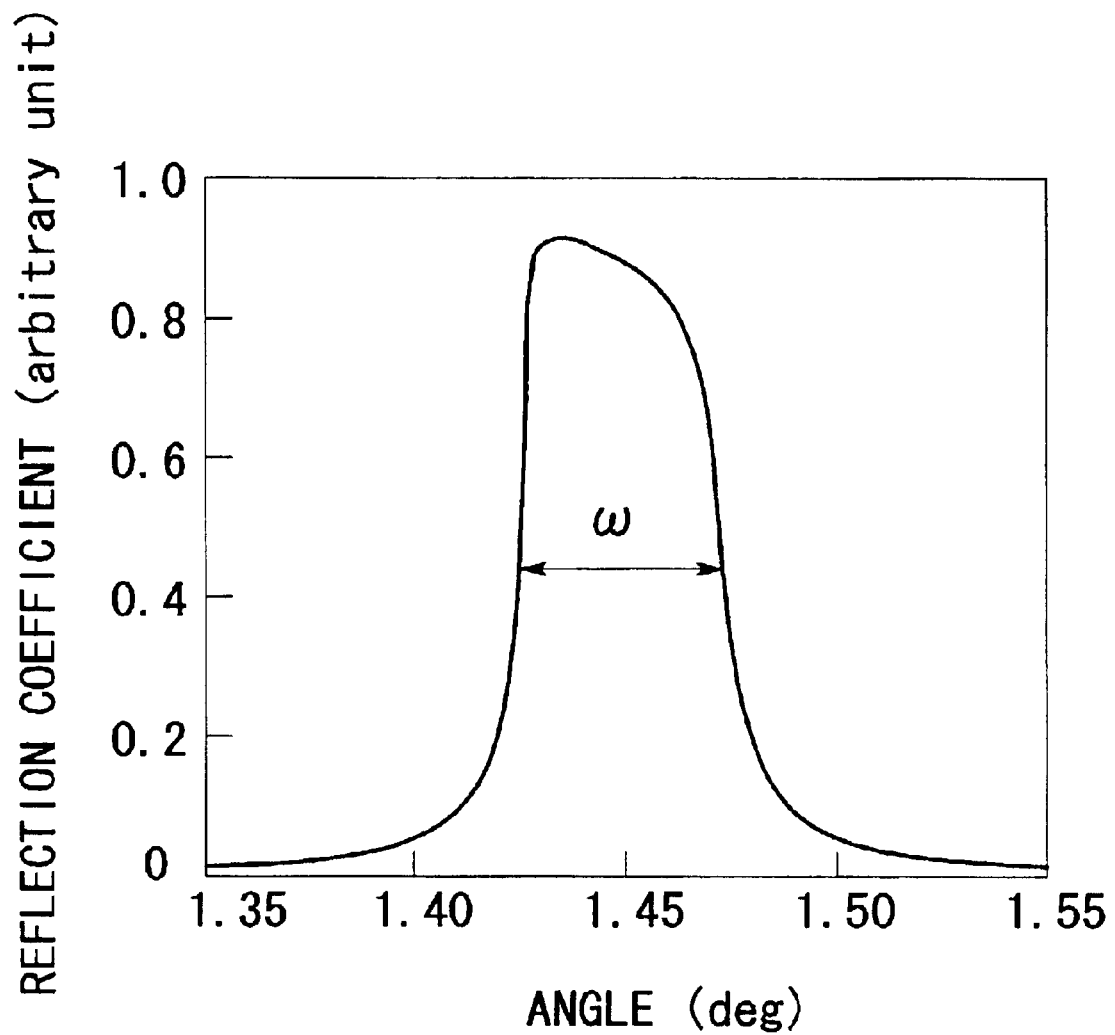
FIG. 6 is a graph showing a reflection coefficient curve of the reflection surface of the elliptic monochromator.

The elliptic monochromator has a reflection surface whose reflection property is shown in FIG. 6. This reflection coefficient curve has a finite width ω of angle (full width at half maximum of the peak, FWHM). If the incidence angle of X-rays becomes within the angle width ω, the X-rays will be reflected by the reflection surface. The angle width ω is referred to hereafter an acceptable receiving angle. If the incidence X-rays have an angle width (i.e., the breadth of the incidence angle) less than the acceptable receiving angle ω, all of the incidence X-rays will be reflected, but if more than the acceptable receiving angle ω, a part of the incidence X-rays will not be reflected. The X-rays from the X-ray source would be captured by the elliptic monochromator with the best efficiency under the condition that the elliptic monochromator is close to the X-ray source so that the incidence X-rays have an angle width (i.e., the breadth of the incidence angle) which equals the acceptable receiving angle ω. Referring to FIG. 5, assuming that the effective focal spot size of the X-ray source is t, the distance between the X-ray source and the reflection point on the monochromator is L3, and the acceptable receiving angle of the monochromator is ω, when an equation of L3=t/ω (where, ω is measured in radian) is satisfied, the angle width of the incidence X-rays will equal the acceptable receiving angle ω. Therefore, it is most efficient that the relationship between L3 and t are selected so as to satisfy the equation mentioned above. For example, with the conditions that ω is 0.05 degrees and the effective focal spot size t is 0.1 mm, L3 should be about 114 mm. If the center of the monochromator is apart from the X-ray source by 114 mm, the front end (i.e., the end closest to the X-ray source) of the monochromator will be apart from the X-ray source by 74 mm, because the length of the monochromator is 80 mm and 114 mm minus 40 mm (half of 80 mm) equals 74 mm.

(4) Relationship Between Shape of and Incidence Angle θ

Figure 7:
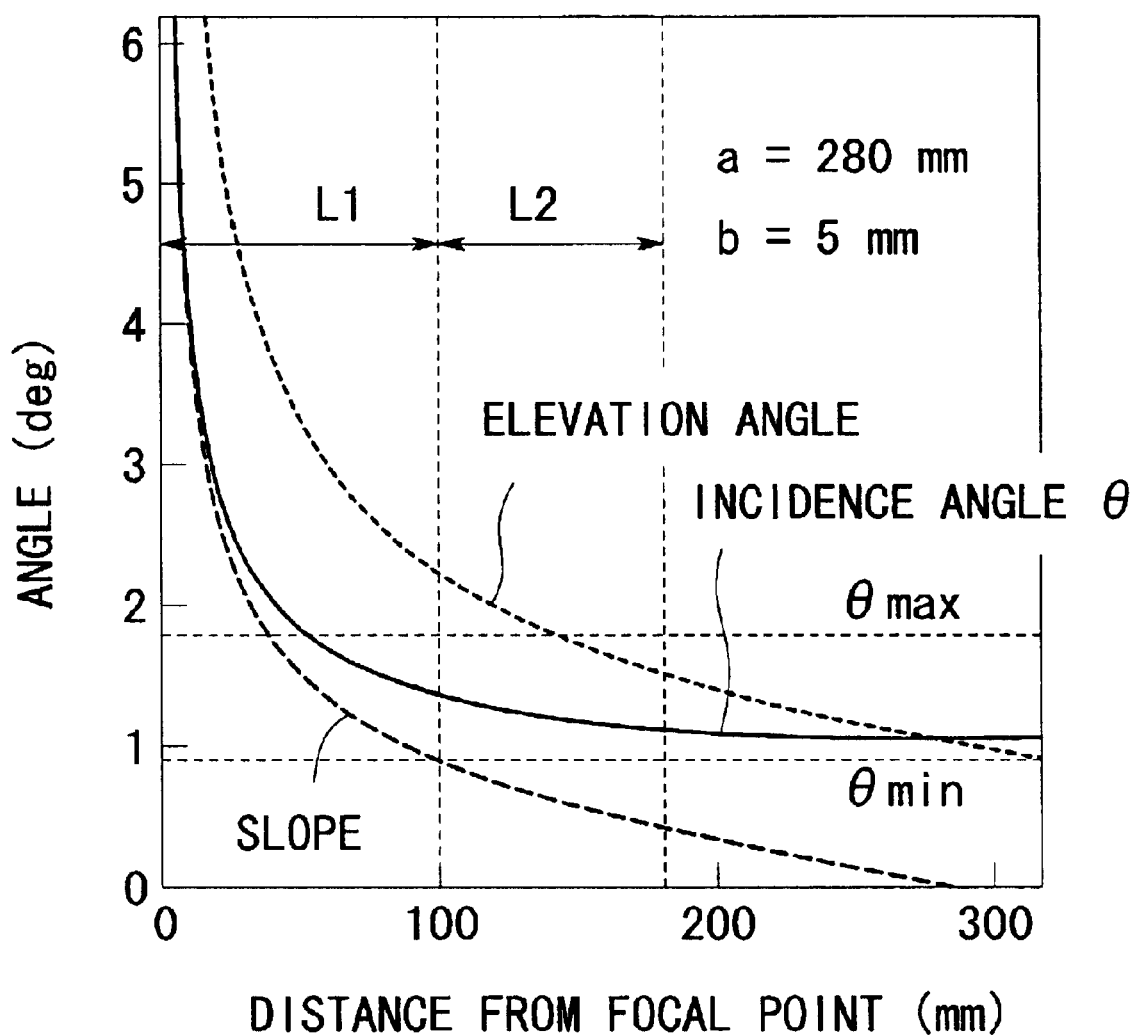
FIG. 7 is a graph showing variation of the incidence angle with a position on the ellipse.
Figure 8:
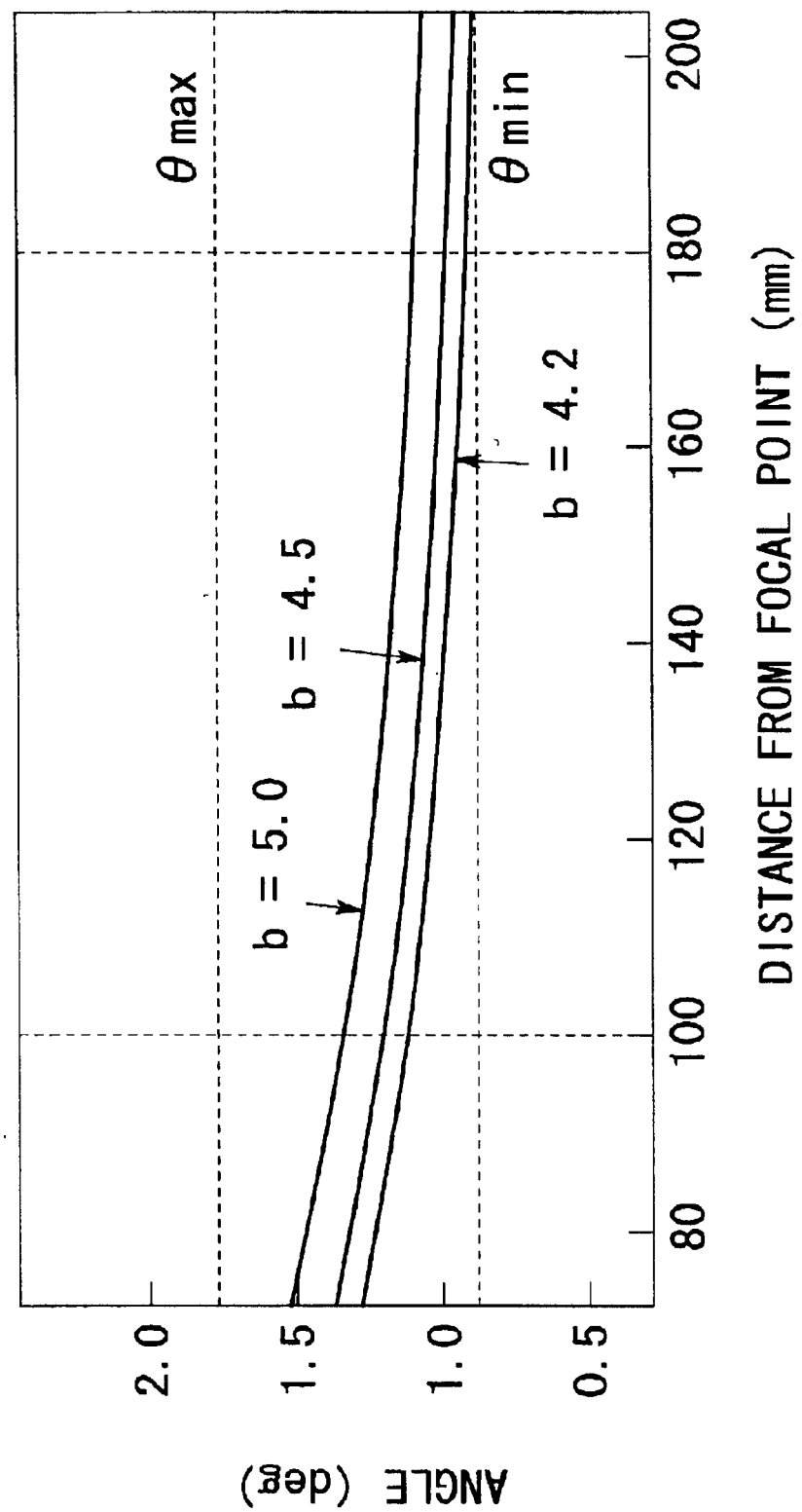
FIG. 8 is an enlarged view of the graph shown in FIG. 7.

Referring to FIG. 4, with the X-Y coordinates shown in the figure, the equation of the ellipse 30 becomes an equation (3) in FIG. 15. The derivative of the equation (3) gives an equation (4) which indicates the slope at each point on the ellipse 30 (i.e., the slope of the tangent to the ellipse). Expressing the slope in degree, the slope at each point on the ellipse 30 becomes an equation (5). On the other hand, the elevation angle (i.e., the angle with respect to the X-ray coordinate) as seen from the focal point F1 toward each point of the ellipse 30 is expressed by an equation (6) in FIG. 15, where f is, as shown in FIG. 4, the distance between the focal point F1 and the origin of the coordinates. The X-ray incidence angle θ at each point on the ellipse 30 is calculated by subtracting the slope of the equation (5) from the elevation angle of the equation (6), resulting in an equation (7) FIG. 7 shows curves of the slope of the equation (5), the elevation angle of the equation (6) and the incidence angle θ of the equation (7). Although the horizontal coordinate of FIG. 7 should be expressed strictly as "distance from coordinates' origin" at each point on the ellipse, it may be expressed as "distance from focal point" because the shape of the actual ellipse is extremely compressed with the coordinates' origin which is very close to the focal point F1. Therefore, the horizontal coordinate is expressed as "distance from focal point". The vertical coordinate indicates an angle which is measured in degree. The graph indicates θmax and θmin too, which are determined under the d-spacing restriction of the synthetic multilayered thin film as mentioned above, θmax being obtained from the equation (9) and θmin being obtained from the equation (10) in FIG. 16. With the ellipse having a certain major axis "a" and a certain minor axis b, if the incidence angle θ at each point on the ellipse becomes between θmax and θmin, as shown in FIG. 7, over the full length L2 of the elliptic monochromator (i.e., the distance from the focal point is within a range of 100 to 180 mm), the restriction of the synthetic multilayered thin film would be satisfied, noting that the graph of FIG. 7 is derived from calculation with the major axis "a" of the ellipse being 280 mm and the minor axis b being 5 mm. The graph of FIG. 8 is an enlarged graph of FIG. 7, showing a region of 100 to 180 mm in the distance from the focal point and indicating the variation of the incidence angle with the minor axis b. That is, when the minor axis b varies as 5.0 mm, 4.5 mm and 4.2 mm, the incidence angle θ varies as shown in FIG. 8, where the incidence angle θ resides between θmax and θmin with any value of the minor axis b.

(5) Relationship Between Irradiation Spot Size on sample and Position of Monochromator Referring to FIG. 4, the sample is to be disposed at the second focal point F2 and it is preferable that the X-ray irradiation spot size on the sample is less than 0.3 mm and the convergence angle β is less than 0.2 degrees. Assuming that the distance between the first focal point F1 and the center of the monochromator 26 is L4 and the distance between the second focal point F2 and the center of the monochromator 26 is L5, the X-ray irradiation spot size on the sample equals (L5/L4) times "effective focal spot size t" of the X-ray source. For example, when t is 0.1 mm and L5 is three times L4, the X-ray irradiation spot size on the sample becomes 0.3 mm. With the stationary ellipse 30, the closer to the X-ray source the elliptic monochromator 26 moves along the ellipse 30, the larger the irradiation spot size on the sample. On the contrary, the farther from the X-ray source the monochromator moves, the smaller the irradiation spot size.

Figure 17:
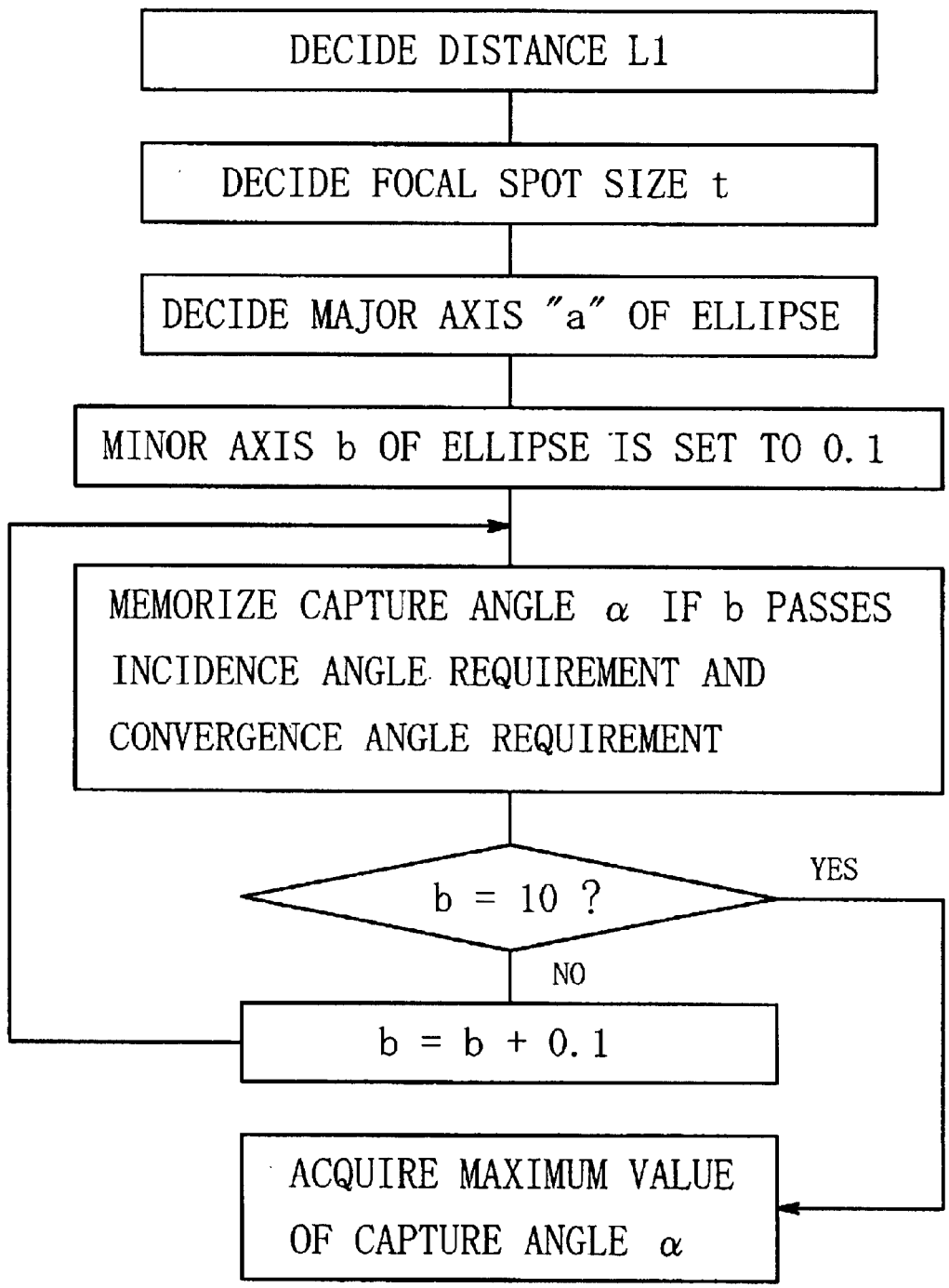
FIG. 17 is a flow chart showing the procedure to obtain the maximum capture angle a for each focal spot size.

Next, one embodiment of detailed procedure to obtain the maximum focal spot size will be described. The maximum focal spot size is defined as the spot size with which the X-ray intensity on the sample becomes maximum. Referring to FIG. 17, this flow chart indicates the procedure which determines, for one combination of the distance L1 and the focal spot size t, the shape of the ellipse (i.e., the major axis "a" and the minor axis b) so that the maximum capture angle α is expected, the value of the maximum capture angle α being also determined at the same time.

First, the distance L1 in FIG. 1 (i.e., the distance between the X-ray focal point and the front end of the composite monochromator 22) must be selected. Since the present invention has an object to realize a higher X-ray intensity on the sample, it is important basically that the composite monochromator 22 is disposed as close as possible to the X-ray source so as to increase the X-ray capture angle α. Therefore, the distance L1 must be less than 100 mm. On the other hand, with the rotating target X-ray tube, the distance between the focal spot on the target and the beryllium window 20 can not be decreased to a value less than a certain limit. As a matter of course, the distance L1 between the focal spot on the target and the front end of the composite monochromator can not be decreased to the certain limit. The minimum value of the distance L1 would be generally 60 mm, and it might be minimized to 40 mm with a special structure of the X-ray source. Therefore, the distance L1 is set within a range of 40 to 100 mm to calculate the optimum focal spot size. Incidentally, as discussed in the above-described "REQUIREMENT REGARDING ACCEPTABLE RECEIVING ANGLE OF REFLECTIION SURFACE", under the conditions that ω is 0.05 degrees and the effective focal spot size is 0.1 mm, the distance L1 is set to preferably about 74 mm so that the X-rays are captured by the elliptic monochromator with the highest efficiency. Consequently, the distance L1 within the range of 40 to 100 mm would be reasonable in view of the acceptable receiving angle, although it would depend on the focal spot size.

The actual calculation selects, for the distance L1, four values: 100 mm, 80 mm, 60 mm and 40 mm. The following description uses 80 mm for the distance L1 for example. Then, in the flow chart of FIG. 17, the distance L1 is set to 80 mm and the procedure moves to the next step "decide focal spot size t". The step selects, for the focal spot size t, one of twenty values from 0.01 mm to 0.4 mm (see the column t in the table of FIG. 18) to calculate the maximum capture angle α for each value of the focal spot size. Then, the focal spot size t is set first to 0.01 mm, resulting in a combination of L1 of 80 mm and t of 0.01 mm.

Next, the procedure moves to the step "decide major axis "a" of ellipse". The major axis "a" of the ellipse should be determined taking in account the irradiation spot size on the sample. As has been described with referring to FIG. 4, it is preferable that the X-ray irradiation spot size on the sample is less than 0.3 mm. With the effective focal spot size t of 0.01 mm, the irradiation spot size less than 0.3 mm is attainable under a condition that L4/L5 is less than 1/30. Then, since L4 equals the sum of L1 and 40 mm and thus equals 120 mm, L5 should be less than 3,600 mm. Since the major axis "a" of the ellipse equals substantially the sum of L4 and L5, "a" must be less than 3,720 mm. In the calculation in this embodiment, "a" is set to 1,860 mm (see the table in FIG. 18).

Next, the procedure moves to the step "minor axis b of ellipse is set to 0.1". The minor axis b of the ellipse is to vary within a range of 0.1 mm to 10 mm in increments of 0.1 mm in the procedure. The capture angle α will be calculated for each value of the minor axis b and it will be determined what is the optimum minor axis b to expect the maximum capture angle α and what is the maximum value of the capture angle α. Now, b is set first to 0.1 mm, resulting in a combination of the major axis "a" and the minor axis b, and we can calculate the curve of the incidence angle θ in the graph of FIG. 7. Within the range of 80 to 160 mm in the distance from the focal spot (i.e., within the range of the monochromator), if the curve of the incidence angle θ resides between θmax and θmin, the b value passes the incidence angle requirement. Since the position and the shape of the elliptic monochromator have been determined, the capture angle α and the convergence angle β both shown in FIG. 4 can be calculated. If the convergence angle β is less than 0.2 degrees, the b value passes the convergence angle requirement too. If the b value passes both of the incidence angle requirement and the convergence angle requirement, a combination of the calculated capture angle α and the value of the minor axis b is memorized. These actions corresponds to the step "memorize capture angle α if b passes incidence angle requirement and convergence angle requirement". On the contrary, if the b value does not pass at least one of the two requirements, the calculated capture angle α is not memorized because the b value is not usable.

Next, the procedure moves to the judgement step "b=10?". If b does not reach 10 mm, then the procedure executes the step "b=b+0.1" and repeats the step "memorize capture angle α if b passes incidence angle requirement and convergence angle requirement". If b reaches 10 mm, the procedure moves to the step "acquire maximum value of capture angle α" which acquires the maximum value among the memorized capture angles α along with the b value corresponding to the maximum value. When the above-mentioned calculations have been completed, one set of data in a row including t=0.01 in the table of FIG. 18 have been completed. In the table, t, a, b and L4 are measured in millimeter and α squared is measured in steradian. When t=0.01 mm, a set of the major axis "a" of 1,860 mm and the minor axis b of 10 mm gives the maximum capture angle α, the maximum α squared, which is measured in steradian, being 1.18869 times 10 to the negative fourth power. The expression "E-4" in the table means "10 to the negative fourth power". With the use of the composite monochromator, X-rays are reflected by the two elliptic monochromators sequentially as shown in FIG. 3 and thereafter focused on the sample, so that the capture angle α squared would be proportional to the X-ray intensity on the sample. Thus, the table indicates the capture angle α squared. L4 in the table is L4 shown in FIG. 4 and equals the sum of L1 and 40 mm. It is found that when t is more than 0.15 mm L4 exceeds 120 mm, because holding the condition of L1=80 mm does not satisfy other requirements (i.e., the incidence angle requirement and the convergence angle requirement) and thus L1 has been altered.

Figure 11:
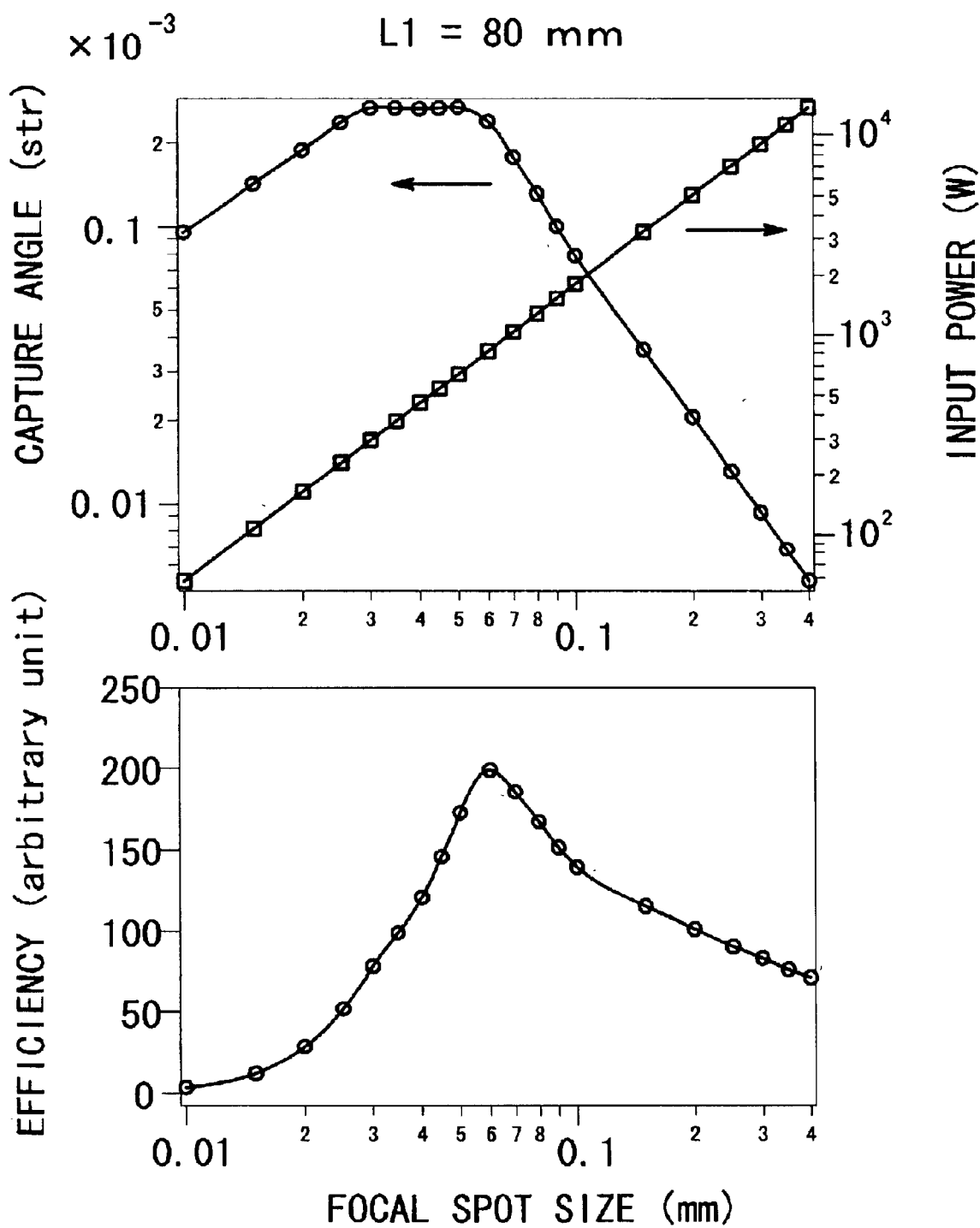
FIG. 11 is a graph showing an efficiency at L1=80 mm.

The values of the capture angle α squared shown in the table of FIG. 18 are expressed as a curve of "capture angle (str)" which is shown in the upper graph of FIG. 11, the vertical coordinate representing the capture angle α squared and the horizontal coordinate representing the focal spot size t. The upper graph of FIG. 11 shows another curve of "input power (W)" which equals the curve of FIG. 9. The lower graph of FIG. 11 shows a curve which is given by multiplying the capture angle curve by the input power curve both shown in the upper graph. Since the product of the capture angle α squared and the input power would be proportional to the X-ray irradiation intensity on the sample, the product is referred to as an "efficiency". The efficiency varies with the focal spot size t and it is found that there is the maximum value or the peak value of the curve. In the graph, when L1=80 mm, the focal spot size of 60 micrometers gives the maximum efficiency. Assuming that the region down to 25 percent loss of the maximum efficiency would be usable practically, the highest efficiency would be expected when the focal spot size is within a range of about 40 to 90 micrometers.

Figure 10:
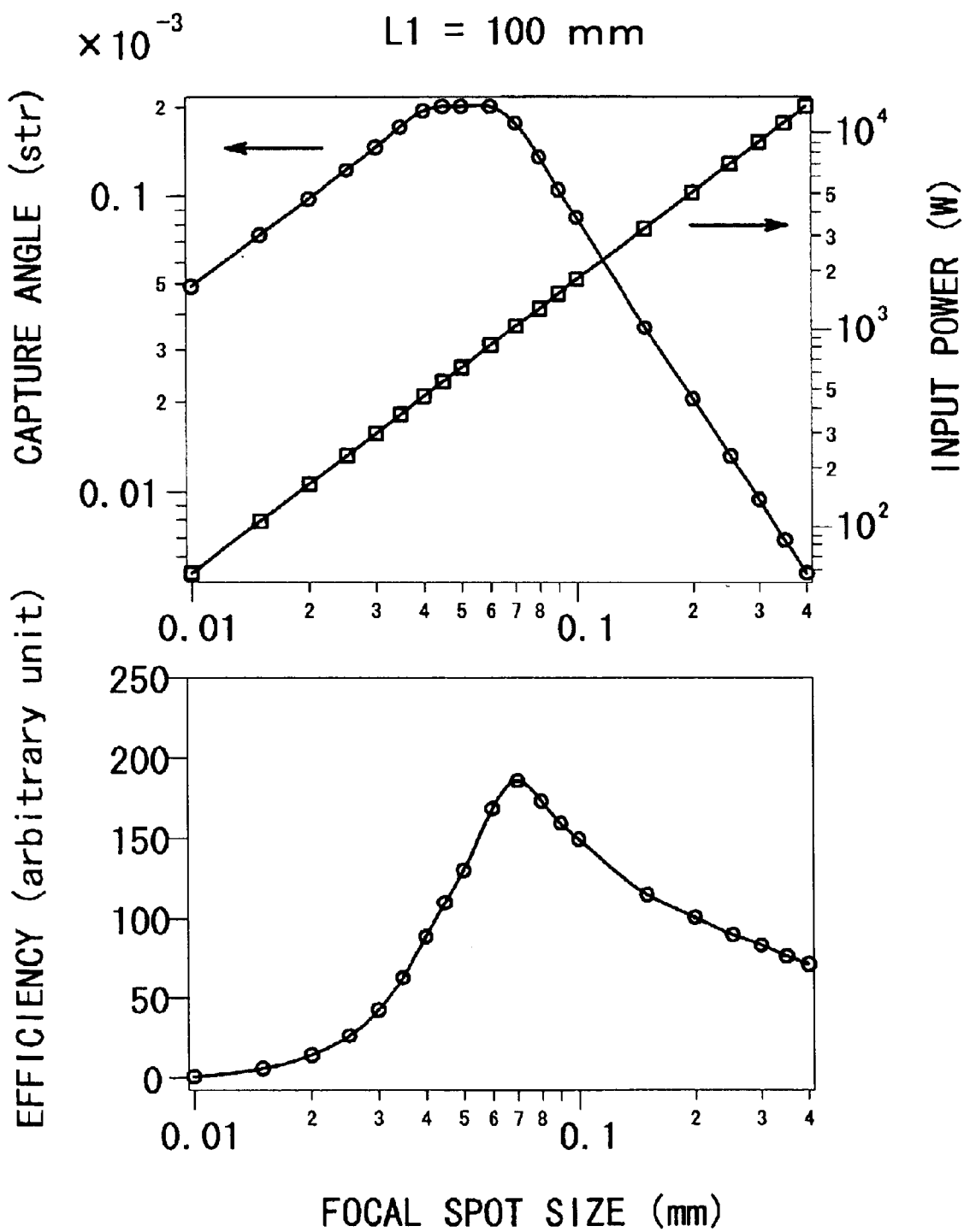
FIG. 10 is a graph showing an efficiency at L1=100 mm.
Figure 12:
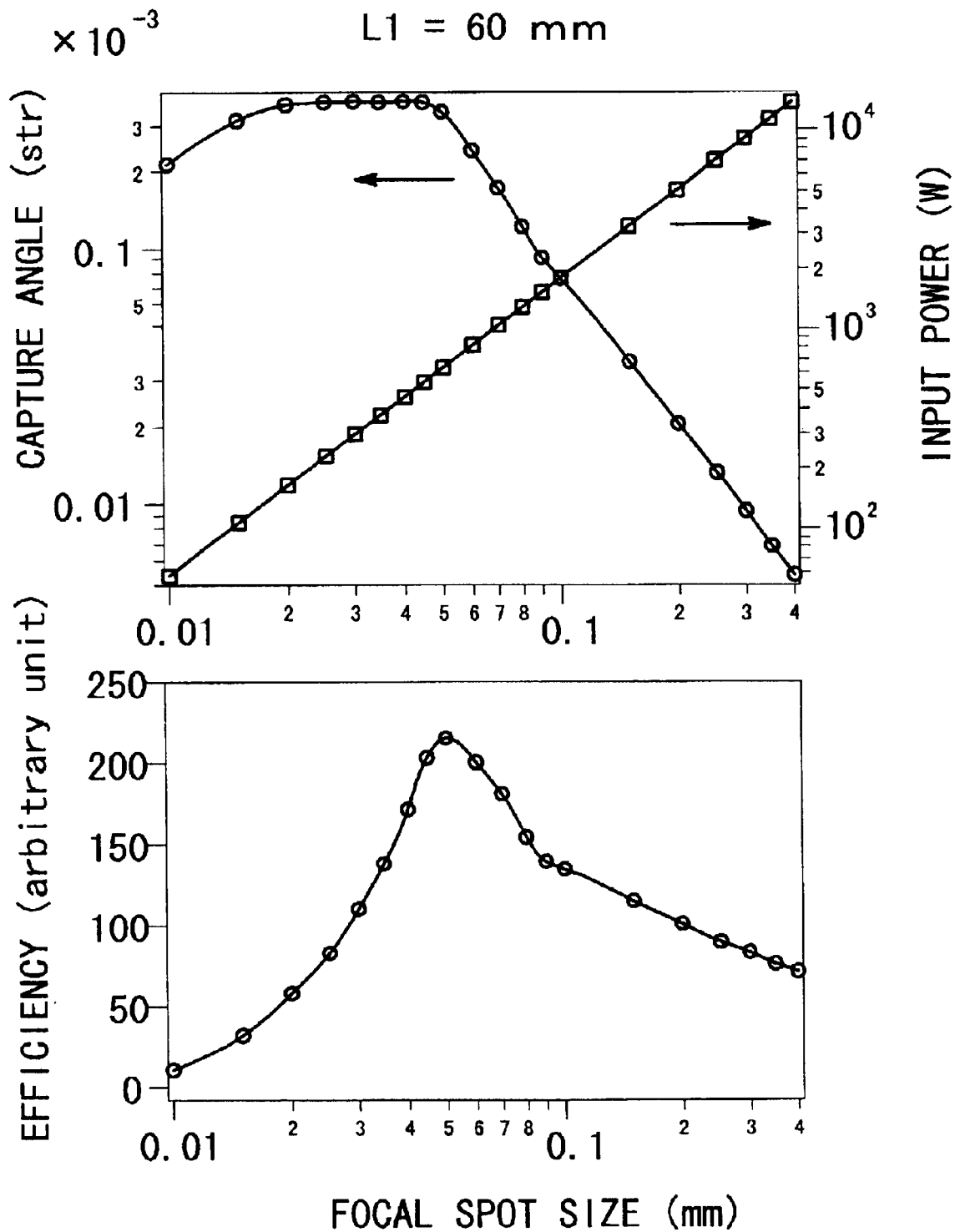
FIG. 12 is a graph showing an efficiency at L1=60 mm.
Figure 13:
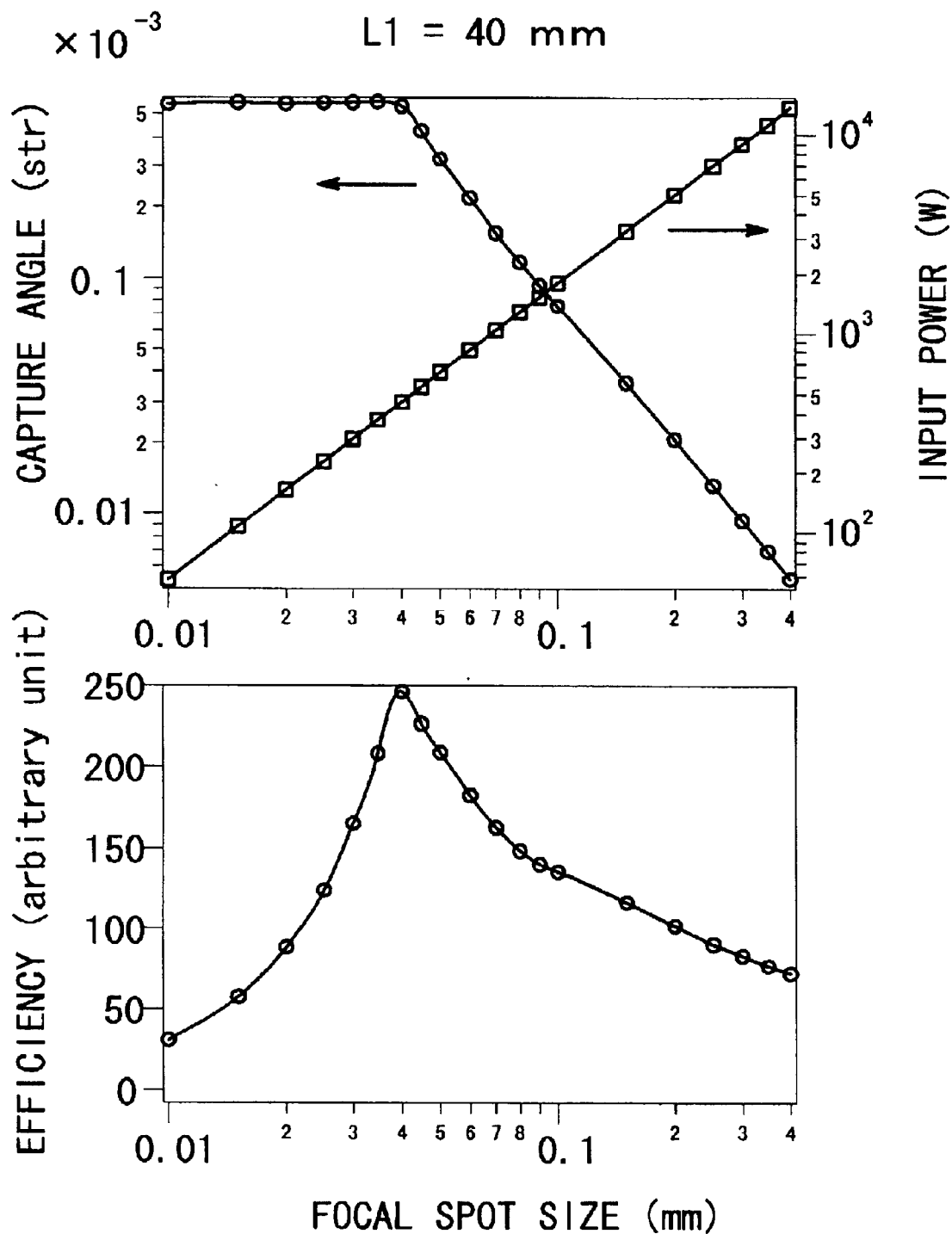
FIG. 13 is a graph showing an efficiency at L1=40 mm.

Similar graphs for L1=100 mm, 60 mm and 40 mm can be calculated and are shown in FIGS. 10, 12 and 13. In FIG. 10, when L1=100 mm, the focal spot size of 70 micrometers gives the maximum efficiency and the practical highest efficiency would be expected within a range of about 60 to 100 micrometers. In FIG. 12, when L1=60 mm, the focal spot size of 50 micrometers gives the maximum efficiency and the practical highest efficiency would be expected within a range of about 40 to 80 micrometers. In FIG. 13, when L1=40 mm, the focal spot size of 40 micrometers gives the maximum efficiency and the practical highest efficiency would be expected within a range of about 30 to 70 micrometers.

It is noted that the focal spot size of 30 micrometers gives a good efficiency only when L1=40 mm (this value is very difficult to realize in the rotating target X-ray tube) but does not give a good efficiency when L1=60 to 100 mm. Therefore, it can be said that the focal spot size of 40 to 100 micrometers gives a good efficiency over a range of 40 to 100 mm in L1.

What is claimed is:

1. Apparatus for X-ray analysis having an X-ray source generating an X-ray beam which is reflected by monochromator means and is to be incident on a sample, characterized in that:

(a) said X-ray source is a rotating target X-ray tube having a rotating target which has an effective focal spot size of 40 to 100 micrometers, (b) said monochromator means is a composite monochromator having a first elliptic monochromator and a second elliptic monochromator joined with each other side by side, (c) each of said elliptic monochromators has a first focal point at which an X-ray focal spot on said target is disposed and a second focal point at which said sample is to be disposed, (d) each of said elliptic monochromators has a reflection surface made of a synthetic multilayered thin film in which layer boundaries, which contribute to diffraction, are parallel to said reflection surface and d-spacing varies continuously along an elliptic-arc so as to satisfy a Bragg's equation for X-rays with a predetermined wavelength at any point of said reflection surface, and (e) a shortest distance between said X-ray focal spot on said target and said composite monochromator is 40 to 100 mm.

2. Apparatus for X-ray analysis according to claim 1, wherein said d-spacing of said synthetic multilayered thin film is within a range of 2.5 to 5.0 nanometers.

3. Apparatus for X-ray analysis according to claim 1, wherein an X-ray irradiation spot size on said sample, which is disposed at said second focal point of each of said elliptic monochromators, is less than 0.3 mm.

4. Apparatus for X-ray analysis according to claim 1, wherein an X-ray convergence angle at said second focal point of each of said elliptic monochromators is less than 0.2 degrees.

5. Apparatus for X-ray analysis having an X-ray source generating an X-ray beam which is reflected by monochromator means, characterized in that:

(a) said X-ray source is a rotating target X-ray tube having a rotating target which has an effective focal spot size of 40 to 100 micrometers, (b) said monochromator means is a composite monochromator having a first elliptic monochromator and a second elliptic monochromator joined with each other side by side, (c) each of said elliptic monochromators has a first focal point at which an X-ray focal spot on said target is disposed, (d) each of said elliptic monochromators has a reflection surface made of a synthetic multilayered thin film in which layer boundaries, which contribute to diffraction, are parallel to said reflection surface and d-spacing varies continuously along an elliptic-arc so as to satisfy a Bragg's equation for X-rays with a predetermined wavelength at any point of said reflection surface, and (e) a shortest distance between said X-ray focal spot on said target and said composite monochromator is 40 to 100 mm.

6. Apparatus for supplying X-rays according to claim 5, wherein said d-spacing of said synthetic multilayered thin film is within a range of 2.5 to 5.0 nanometers.

7. Apparatus for supplying X-rays according to claim 5, wherein an X-ray irradiation spot size on said sample, which is disposed at said second focal point of each of said elliptic monochromators, is less than 0.3 mm.

8. Apparatus for supplying X-rays according to claim 5, wherein an X-ray convergence angle at said second focal point of each of said elliptic monochromators is less than 0.2 degrees.

* * * * *